United States Patent [19]

Tsuneno et al.

[11] Patent Number: 4,515,725

[45] Date of Patent: May 7, 1985

[54] PROCESS FOR PREPARING BORIC ESTERS OF GLYCEROL FATTY ACID ESTERS

[75] Inventors: Tatsuro Tsuneno, Wakayama; Masaaki Takaku, Oosaka, both of Japan

[73] Assignee: Kao Corporation, Tokyo, Japan

[21] Appl. No.: 517,439

[22] Filed: Jul. 26, 1983

[30] Foreign Application Priority Data

Aug. 3, 1982 [JP] Japan ................................. 57-135374

[51] Int. Cl.$^3$ ............................................... C11C 3/02
[52] U.S. Cl. ................................................. 260/410.7
[58] Field of Search ......................... 260/410.7, 410 R

[56] References Cited

U.S. PATENT DOCUMENTS

| | | | |
|---|---|---|---|
| 2,484,979 | 10/1949 | Barsky | 260/410.7 |
| 2,509,413 | 5/1950 | Barsky | 260/410.7 |
| 3,117,089 | 1/1964 | De Young | 260/410.7 |
| 3,150,157 | 9/1964 | Liao | 260/410 R |
| 3,373,170 | 3/1968 | Jones | 260/410.7 |

*Primary Examiner*—Helen M. S. Sneed
*Attorney, Agent, or Firm*—Oblon, Fisher, Spivak, McClelland & Maier

[57] ABSTRACT

Preparation of boric esters of glycerol fatty acid esters which comprises reacting triglycerides such as natural oils and fats with glycerol and boric acid in specific ratios.

3 mols of boric acid, 1 to 2 mols of at least one long-chain fatty acid triglyceride, and 4 to 5 mols of glycerol are interacted under neutral or acidic conditions at a temperature of 240°–280° C.

According to the invention, boric esters can be obtained substantially in quantitative and good yield because of a small loss of reaction.

3 Claims, No Drawings

PROCESS FOR PREPARING BORIC ESTERS OF GLYCEROL FATTY ACID ESTERS

BACKGROUND OF THE INVENTION

1. Field of the Invention

This invention relates to a novel process for the preparation of boric esters of glycerol fatty acid esters. More particularly, it relates to a process for the preparation of boric esters of glycerol fatty acid esters which comprises reacting triglycerides such as natural oils and fats with glycerol and boric acid in specific ratios.

2. Description of the Prior Art

These materials are known as a substance having surface activity and are useful as an antistatic agent or emulsifier.

Several processes of preparing boric esters of glycerol fatty acid esters are known including (1) a process in which glycerol and boric acid are heated for dehydration reaction to obtain a boric triester, and then the remaining hydroxyl groups of the triester are thermally dehydrated using fatty acids or are thermally dealcoholized using lower alcohol esters such as methyl esters of fatty acids thereby achieving the esterification of fatty acids, (2) a process in which fatty acid glycerol monoesters or mixtures thereof with glycerol are reacted and dehydrated with boric acid under heating conditions (Japanese Patent Publication Nos. 46-31847 and 53-39413), and the like.

However, these processes make use of fatty acids, lower alcohols of fatty acids, or fatty acid glycerol monoesters derived from oils and fats, thus requiring a number of very complicate steps.

SUMMARY OF THE INVENTION

We have made intensive studies to develop a process of more efficiently and more simply preparing boric esters of glycerol fatty acid esters. As a result, it was found that boric esters of glycerol fatty acid esters (hereinafter referred to simply as boric esters) could be directly produced from fatty acid triglycerides such as natural oils and fats.

According to the present invention, there is provided a process for preparing a boric ester of a glycerol fatty acid ester which is characterized by interacting 3 mols of boric acid, 1 to 2 mols of at least one long-chain fatty acid triglyceride, and 4 to 5 mols of glycerol under neutral or acidic conditions at a temperature of 240° to 280° C.

DETAILED DESCRIPTION OF THE INVENTION AND PREFERRED EMBODIMENTS

In order to carry out the process of the invention, at least one long-chain triglyceride such as natural oils or fats, glycerol, and boric acid in the above-defined mixing ratios may be simultaneously charged and heated for reaction. Alternatively, glycerol and boric acid in the defined mixing ratio may be first esterified and dehydrated under heating conditions, to which long-chain fatty acid triglycerides such as oils and fats are added and heated for a subsequent reaction. The reaction is effected such that the reactants are sufficiently agitated at a temperature of 240° to 280° C. for a period of about 1 to 10 hours, preferably 3 to 6 hours, while heating and dehydrating, if necessary, in an atmosphere of an inert gas such as nitrogen gas.

The long-chain triglycerides used as one of the starting materials of the invention are triesters of long-chain fatty acids and glycerol. Natural oils and fats or synthetic esters are used. The fatty acid moiety should preferably be saturated or unsaturated and have 8 to 22 carbon atoms. Most preferable examples of the triglycerides include animal oils such as beef tallow, lard and the like, and plant oils such as rape seed oil, cotton seed oil, soybean oil and the like. Especially, natural oils and fats containing residues of oleic acid and linoleic acid are preferable.

The boric esters obtained according to the process of the invention are compounds of the following general formulas. In general, the boric esters are obtained in the form of mixtures of various compounds of the formulas.

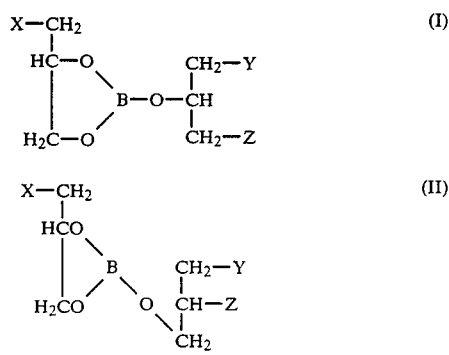

in which X, Y, and Z independently represent an OH group or a

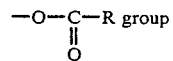

provided that at least one of X, Y, and Z is a

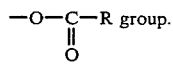

R is a saturated or unsaturated alkyl or alkenyl group having 7 to 23 carbon atoms.

As will become apparent from the above, it is not necessary according to the invention that fatty acid triglycerides such as natural oils and fats are converted such as by hydrolysis into fatty acids and lower alcohols esters of fatty acids, followed by reaction with boric acid. In other words, fatty acid triglycerides such as natural oils and fats can be directly reacted with glycerol and boric acid under limited conditions thereby quantitatively producing boric esters in high yield.

In the process of the invention, it is unnecessary to remove low boiling alcohols such as methyl alcohol from the reaction system as in the known processes. The process of the invention has another advantage that the water produced by the reaction can be reduced by 25% over the known processes. The process of the invention is further advantageous in that a large number of starting materials are used, intended products can be obtained substantially in quantitative yield because of a small loss of reaction, and products can be directly obtained from inexpensive oils and fats by only one reaction step, thus the process being very efficient and economical. In addition, the process of the invention can also be applied to oils and fats having a number of unsaturated groups which are difficult in producing corresponding fatty acids.

The present invention is described by way of example.

EXAMPLE 1

20.1 g (0.32 mol) of boric acid was charged into a mixture of 97 g (0.11 mol) of rape seed oil (IV: 120) and 50 g (0.54 mol) of glycerol, followed by reaction at a temperature of 255° to 265° C. for 5 hours in an atmosphere of nitrogen and removal of 17.5 g of the water produced by the reaction, thereby obtaining a product having an acid value of 133.

The product was analysed with the result that it had a composition comprising a mixture of 50%, based on rough molar ratio, of boric esters of the general formulas (I) and (II) in which one of X, Y, and Z is an $RCO_2$ group and the other two are independently hydroxyl group, about 25% of boric esters of the formulas in which two of X, Y, and Z are independently an $RCO_2$ group and the other is a hydroxyl group, about 25% of boric esters of the formulas in which all X, Y, and Z are independently a hydroxyl group, and a small amount of boric esters of the formulas in which X, Y, and Z are all an $RCO_2$ group.

EXAMPLE 2

24.1 g (0.39 mol) of boric acid was charged into a mixture of 116.4 g (0.13 mol) of rape seed oil (IV: 77) and 60 g (0.65 mol) of glycerol, followed by reaction at a temperature of 255° to 265° C. for 5 hours in an atmosphere of nitrogen and removal of 23 g of the water produced by the reaction. As a result, there was obtained a product having an acid value of 129.

The product was analysed with the result that it had a composition similar to that of Example 1 except for the type of long-chain alkyl group.

EXAMPLE 3

20.1 g (0.32 mol) of boric acid was charged into a mixture of 94 g (0.11 mol) of cotton seed oil (IV:112) and 50 g (0.54 mol) of glycerol, followed by reaction at a temperature of 255° to 265° C. for 6 hours in an atmosphere of nitrogen and removal of 18 g of the water produced by the reaction. The resulting product had an acid value of 135.

The product was analysed with the result that it had a composition similar to that of Example 1 except for the type of long-chain alkyl group.

EXAMPLE 4

20.1 g (0.32 mol) of boric acid was charged into a mixture of 93 g (0.11 mol) of soybean oil (IV:120) and 50 g (0.54 mol) of glycerol, followed by reaction at a temperature of 255° to 265° C. for 6 hours in an atomosphere of nitrogen and removal of 16.3 g of the water produced by the reaction. The resulting product had an acid value of 129.

The product was analysed with the result that it had a composition similar to that of Example 1 except for the type of long-chain alkyl group.

EXAMPLE 5

20.1 g (0.32 mol) of boric acid was charged into a mixture of 93 g (0.11 mol) of lard (IV:66) and 50 g (0.54 mol) of glycerol, followed by reaction at a temperature of 260° to 270° C. for 4 hours in an atmosphere of nitrogen and removal of 19.2 g of the water produced by the reaction. The resulting product had an acid value of 125.

The product was analysed with the result that it had a composition similar to that of Example 1 except for the type of long-chain alkyl group.

EXAMPLE 6

13.1 g (0.21 mol) of boric acid was charged into a mixture of 126 g (0.14 mol) of rape seed oil (IV: 120) and 26 g (0.28 mol) of glycerol, followed by reaction at a temperature of 260° to 270° C. for 7 hours in an atmosphere of nitrogen and removal of 12 g of the water produced by the reaction. The resulting product had an acid value of 85.

The product was analysed with the result that it had a composition comprising a mixture of about 50%, based on rough molar ratio, of boric esters of the general formulas (I) and (II) in which two of X, Y, and Z are independently an $RCO_2$ group and the remaining one is independently a hydroxyl group, about 25% of boric esters of the formulas in which one of X, Y, and Z is an $RCO_2$ group and the other two are independently a hydroxyl group, about 25% of boric esters of the formulas in which all X, Y, and Z are independently an $RCO_2$ group, and a small amount of boric esters of the formulas in which X, Y, and Z are all a hydroxyl group.

EXAMPLE 7

35.3 g (0.57 mol) of boric acid was charged into a mixture of 90 g (0.19 mol) of caprylic acid triglyceride and 87 g (0.95 mol) of glycerol, followed by reaction at a temperature of 250° to 260° C. for 7 hours in an atomosphere of nitrogen and removal of 29 g of the water produced by the reaction. The resulting product had an acid value of 180.

The product was analysed with the result that it had a composition similar to that of Example 1 except for the type of long-chain alkyl group.

What is claimed is:

1. A process for preparing a boric ester of a glycerol fatty acid ester which consists essentially in reacting 3 mols of boric acid, 1 to 2 mols of at least one long-chain fatty acid triglyceride, and 4 to 5 mols of glycerol under neutral or acidic conditions at a temperature of 240° to 280° C.

2. A process for preparing a boric ester of a glycerol fatty acid ester according to claim 1, wherein said long-chain fatty acid glyceride has a long-chain fatty acid moiety which is saturated or unsaturated and contains 8 to 22 carbon atoms.

3. A process for preparing a boric acid of a glycerol fatty acid ester according to claim 1, wherein said long-chain fatty acid glyceride is a member selected from the group consisting of natural animal and plant oils and fats.

* * * * *